United States Patent [19]

Platt et al.

[11] Patent Number: 5,525,616
[45] Date of Patent: Jun. 11, 1996

[54] METHOD OF INHIBITING GLYCOLIPID SYNTHESIS

[75] Inventors: Frances M. Platt, Oxford, United Kingdom; Gabrielle R. Neises, Chesterfield, Mo.; Raymond A. Dwek; Terry D. Butters, both of Oxford, United Kingdom

[73] Assignee: Monsanto Company, St. Louis, Mo.

[21] Appl. No.: 439,842

[22] Filed: May 12, 1995

Related U.S. Application Data

[62] Division of Ser. No. 321,718, Oct. 12, 1994, which is a continuation of Ser. No. 61,645, May 13, 1993, Pat. No. 5,399,567.

[51] Int. Cl.⁶ .................... A61K 31/445; C07D 211/46
[52] U.S. Cl. ............................... 514/315; 546/242
[58] Field of Search ........................ 514/315; 546/242

[56] References Cited

U.S. PATENT DOCUMENTS

| | | | |
|---|---|---|---|
| 4,065,562 | 12/1977 | Ohata et al. | 424/267 |
| 4,182,767 | 1/1980 | Mural et al. | 424/267 |
| 4,533,668 | 8/1985 | Matsumara et al. | 514/321 |
| 4,639,436 | 1/1987 | Junge et al. | 514/24 |
| 4,849,430 | 7/1979 | Fleet et al. | 514/315 |
| 5,011,829 | 4/1991 | Hirsch et al. | 514/50 |
| 5,030,638 | 7/1991 | Partis et al. | 514/315 |

FOREIGN PATENT DOCUMENTS

| | | |
|---|---|---|
| 8703903 | 7/1987 | WIPO . |

OTHER PUBLICATIONS

Saunier et al., J. Biol. Chem. 257, 14155–14161 (1982).
Elbein, Ann. Rev. Biochem. 56, 497–534 (1987).
NewBrun, Arch. Oral Biol. 28, 531–536 (1982).
Wang et al., Tetrahedron Lett. 34, 403–406 (1993).
Karlsson et al., J. Biol. Chem. 268, 570–576 (1993).
Shukla et al., Biochem. Biophys. Acta 1083, 101–108 (1991).
Shukla and Radin, J. Lipid Res. 32, 713–722 (1991).
Basu, J. Biol. Chem. 248, 1388–1394 (1973).
van Heyningen, Nature 249, 415–417 (1974).
Karlsson, Ann. Rev. Biochem. 58, 309–350 (1989).
Platt et al., Eur. J. Biochem. 208, 187–193 (1992).
Butters and Hughes, In Vitro 17, 831–838 (1981).
Chem. Abst. 115:250930 "Human Acid β-glucosidase, etc."
Fabbro et al. J. Biol. Chem. (1991) 266(23) 15021–7.
Chem. Abst. 110: 91215 "Human Acid β-glucosidase, etc."
Osiecki-Newman et al., Enzyme (1988), 40(4), 173–88.
Chem. Abst: 108: 18433 "Human Acid β-glucosidase, etc."
Osiecki-Newman et al., Biochim. Biophys. Acta. (1987) 915(1), 87–100.

*Primary Examiner*—Peter O'Sullivan
*Attorney, Agent, or Firm*—Scott J. Meyer

[57] ABSTRACT

A method is disclosed for inhibiting the biosynthesis of glycolipids in cells capable of producing glycolipids comprising subjecting said cells to a glycolipid inhibitory effective amount of an N-alkyl derivative of 1,5-dideoxy-1,5-imino-D-glucitol in which said alkyl contains from 2–8 carbon atoms.

7 Claims, 7 Drawing Sheets

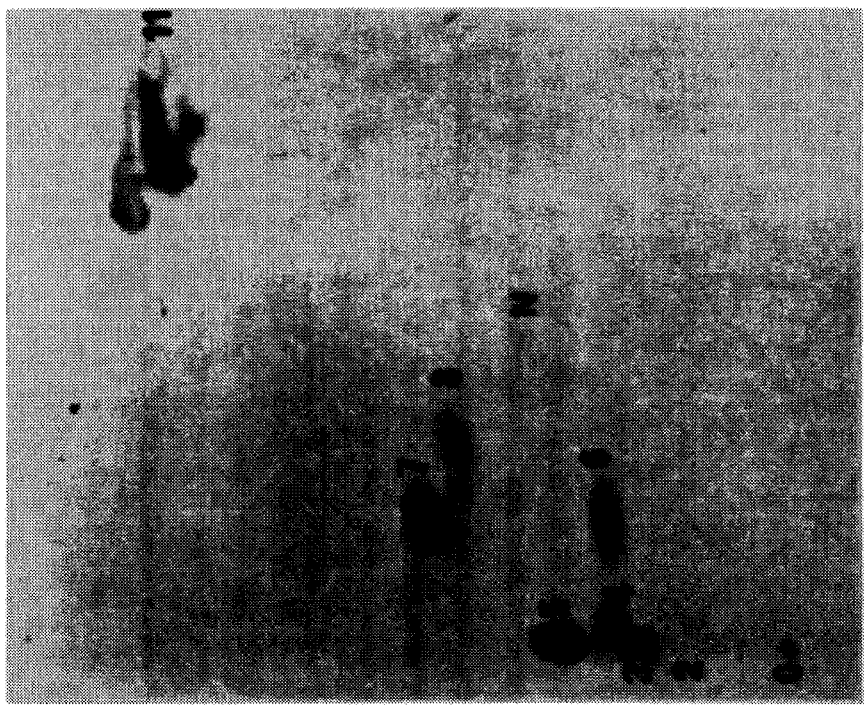
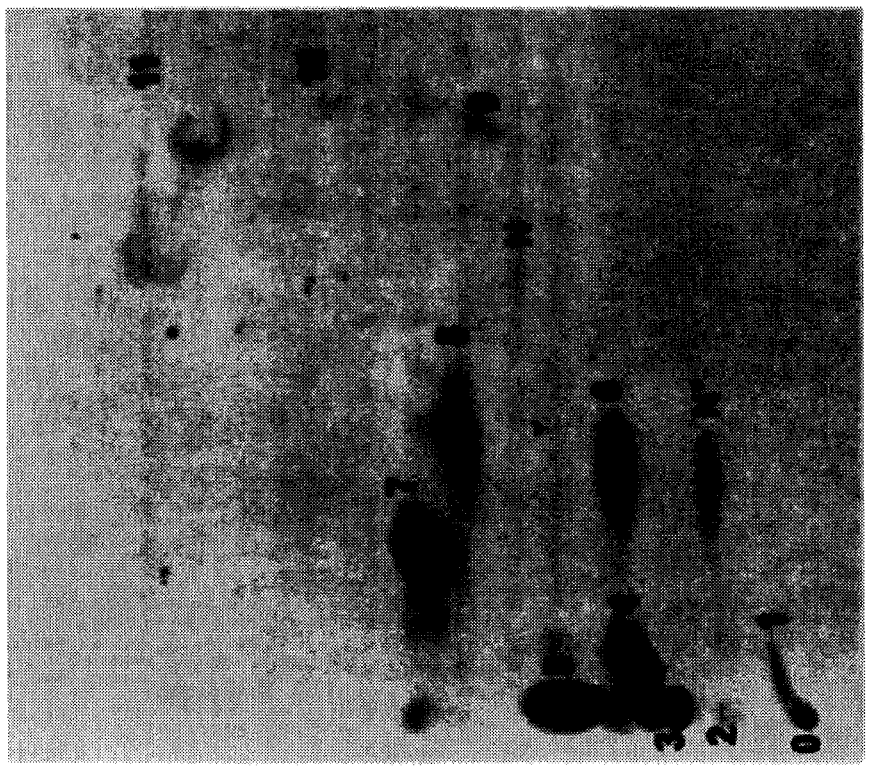
FIG. 6B
FIG. 6A

METHOD OF INHIBITING GLYCOLIPID SYNTHESIS

This is a division of application Ser. No. 08/321,718, filed Oct. 12, 1994, which is a continuation of application Ser. No. 08/061,645, filed May 13, 1993 now U.S. Pat. No. 5,399,567.

BACKGROUND OF THE INVENTION

This invention relates to a novel method of inhibiting glycolipid synthesis and, more particular, to the use of N-alkyl derivatives of 1,5-dideoxy-1,5-imino-D-glucitol for inhibiting glycolipid biosynthesis in cells capable of producing glycolipids, in which said alkyl groups contain from about 2–8 carbon atoms.

1,5-Dideoxy-1,5-imino-D-glucitol (which is also known as 1-deoxynojirimycin or DNJ) and its N-alkyl derivatives are known inhibitors of the N-linked oligosaccharide processing enzymes, α-glucosidase I and II. Saunier et al., *J. Biol. Chem.* 257, 14155–14161 (1982); Elbein, *Ann. Rev. Biochem.* 56, 497–534 (1987). As glucose analogs they also have potential to inhibit glucosyltransferases. Newbrun et al., *Arch. oral Biol.* 28, 516–536 (1983); Wang et al., *Tetrahedron Lett.* 34, 403–406 (1993). Their inhibitory activity against the glucosidases has led to the development of these compounds as antihyperglycemic agents and antiviral agents. See, e.g., PCT Int'l. Appln. WO 87/03903 and U.S. Pat. Nos.: 4,065,562; 4,182,767; 4,533,668; 4,639,436; 4,849,430; 5,011,829;and 5,030,638.

BRIEF DESCRIPTION OF THE INVENTION

In accordance with the present invention, a method is provided for inhibiting the biosynthesis of glycolipids in cells capable of producing glycolipids which comprises treatment of said cells with a glycolipid inhibitory effective amount of an N-alkyl derivative of 1,5-dideoxy-1,5-imino-D-glucitol (DNJ) in which said alkyl contains from 2–8 carbon atoms and preferably from 4–6 carbon atoms. The length of the N-alkyl chain has been found to be important to said inhibitory activity since the non-alkylated DNJ and the N-methyl derivative of DNJ were each found to be inactive for such inhibition. Thus, a minimum alkyl chain length of 2 carbon atoms has been found to be necessary for efficacy.

Illustratively, the N-butyl DNJ was also unexpectedly found to be a substantially more potent inhibitor of glycolipid biosynthesis than it is as an α-glucosidase I inhibitor. That is, it was inhibitory of glycolipid biosynthesis at relatively low concentrations (about 50 µM) compared to the mM level of concentration in cell culture systems for α-glucosidase I inhibition [Karlsson et al., *J. Biol. Chem.* 268, 570–576 (1993)]. Also illustratively, the N-butyl and N-hexyl derivatives of DNJ inhibited the biosynthesis of all glucoceramide based glycosphingolipids.

The inhibitory effect of these compounds on the biosynthesis of glycolipids is illustrated herein in myeloid cell lines (e.g., HL-60 and K-562) as well as in lymphoid cell lines (e.g., MOLT-4 and H9). These are well-known, widely distributed and readily available human cell lines. For example, HL-60 cells are promyelocytic cells described by Collins et al., *Nature* 270, 347–349 (1977). They are also readily available from the American Type Culture Collection, Rockville, Maryland under accession number ATCC CCL 240. K-562 cells are of myeloid origin described by Lozzio and Lozzio, *Blood* 45, 321–324 (1975). They are also readily available from the same depository under accession number ATCC CCL 243. MOLT-4 cells are lymphoid cells described in *J. Nat'l. Cancer Inst.* 49, 891–895 (1972). They are also readily available from the same depository under accession number ATCC CRL 1582. H9 cells are of lymphoid origin described by Gallo and Popovic, *Science* 224, 497–500 (1984). They are also readily available from the same depository under accession number ATCC HTB 176.

The inhibition of glycolipid biosynthesis by these N-alkyl derivatives of DNJ is further demonstrated herein by the reduction of the binding of cholera toxin to these four illustrative cell lines when cultured in the presence on N-butyl DNJ. These compounds thus are also useful as anti-microbial agents by inhibiting the surface expression on glycolipid receptors for bacteria and bacterial toxins as illustrated hereinafter in Tables 1 and 2, respectively.

The inhibitory effect upon the biosynthesis of glycolipids is still further illustrated by the ability of N-butyl DNJ to offset glucoceramide accumulation in a standard, state-of-the-art in vitro model of Gaucher's disease in which the murine macrophage cell line WEHI-3B was cultured in the presence of an irreversible glucocerebrosidase inhibitor, conduritol β epoxide (CBE), to mimic the inherited disorder found in Gaucher's disease. The compound prevents lysosomal glycolipid storage which is useful for the management of this and other glycolipid storage disorders as illustrated hereinafter in Table 3.

Illustratively, the N-butyl-DNJ is also shown herein to be a more effective inhibitor of glycolipid biosynthesis than either PDMP or PPMP. PDMP, which chemically is DL-threo-1-phenyl-2-decanoylamino-3-morpholino-1-propanol, is known to be an effective inhibitor of the glycosyltransferase that makes glucosylceramide. See, for example, Shukla et al., *Biochim. Biophys. Acta* 1083, 101–108 (1991), and Shukla and Radin, *J. Lipid Res.* 32, 713–722 (1991), for reports on this activity of PDMP. Its analog PPMP, chemically is DL-threo-1-phenyl-2-hexadecanoylamino-3-morpholino-1-propanol. Thus, the glycolipid biosynthesis inhibitory activity of N-butyl-DNJ is correlatable to the corresponding activity of conventional compounds in this field.

TABLE 1

| GLYCOSPHINGOLIPID RECEPTORS FOR BACTERIAL CELLS | | |
|---|---|---|
| Microorganism | Target Issue | Presumed Specificity |
| *E. coli* | Urinary | Galα4Galβ |
| *E. coli* | Urinary | GlcNAcβ |
| Propionibacterium | Skin/Intestine | Galβ4Glcβ |
| Several bacteria | Diverse | Galβ4Glcβ |
| *Streptococcus pneumoniae* | Respiratory | GlcNAcβ3Gal |
| *E. coli* CFA/I | Intestine | NeuAcα8 |
| *E. coli* | Urinary | NeuAcα3Gal |
| *E. coli* | Intestine | NeuGcα3Galβ4GlcβCer GalNAcβ4(NeuAcα3)-Galβ4GlcβCer |
| *Staphylococcus saprophyticus* | Urinary | Galβ4GlcNAc |
| *Actinomyces naeslundi* | Mouth | Galβ, GalNAcβ, Galβ3GalNAcβ, GalNacβ3Galβ |
| Pseudomonas | Respiratory | GalNAcβ4Gal |
| *Neisseria gonorrhoeae* | Genital | Galβ4Glcβ NeuAcα3Galβ4GlcNAc |

TABLE 2

GLYCOSPHINGOLIPID RECEPTORS FOR BACTERIAL TOXINS

| Microorganism | Toxin | Target Tissue | Presumed Receptor Sequence |
|---|---|---|---|
| Vibrio chloerae | Cholera toxin | Small Intestine | Galβ3GalNAcβ4-(NeuAcα3)Gal-β4GlcβCer |
| E. coli | Heat-labile toxin | Intestine | Galβ3GalNAcβ4-(NeuAcα3)Gal-β4GlcβCer |
| Clostridium tetani | Tetanus toxin | Nerve | Galβ3GalNAcβ4-(NeuAcα8Neu-Acα3)Galβ4Glc-βCer |
| Clostridium botulinum | Botulinum toxin A and E | Nerve Membrane | NeuAcα8NeuAcα-3Galβ3GalNAcβ-4(NeuAcα8Neu-Acα3)Galβ4Glc-βCer |
| Clostridium botulinum | Botulinum toxin B, C and F | Nerve Membrane | NeuAcα3Galβ3-GalNAβ4(Neu-Acα8NeuAcα3)-Galβ4GlcβCer |
| Clostridium botulinum | Botulinum toxin B | Nerve Membrane | GalβCer |
| Clostridium perfringens | Delta toxin | Cell lytic | GalNAcβ4-(NeuAcα3)Galβ-4GlcβCer |
| Clostridium difficile | Toxin A | Large Intestine | Galα3GalβGlc-NAcβ3Galβ4-GlcβCer |
| Shigella dysenteriae | Shiga toxin | Large Intestine | Galα4GalβCer Galα4Galβ4Glc-βCer GlcNAcβ4Glc-NAc |
| E. coli | Vero toxin or Shiga-like toxin | Intestine | Galα4Galβ4-GlcβCer |

TABLE 3

HEREDITARY GLYCOLIPID STORAGE DISORDERS

| Disease | Lipid Accumulation | Enzyme Defect |
|---|---|---|
| Gaucher's | Glucocerebroside | Glucocerebroside-β-glucosidase |
| Ceramide Lactoside Lipidosis | Ceramide Lactoside | Ceramidelactoside-β-galactosidase |
| Fabry's | Ceramide Trihexoside | Ceramidetrihexoside-α-galactosidase |
| Tay-Sach's | Ganglioside GM2 | Hexosaminidase A |
| Sandhoff's | Globoside and GM2 | Hexosaminidase A and B |
| General Gangliosidosis | Ganglioside GM1 | β-Galactosidase |
| Fucosidosis | H-isoantigen | α-Fucosidase |
| Krabbe's | Galactocerebroside | Galactocerebroside-β-galactosidase |
| Metrachromatic Leukodystrophy | Sulfatide | Sulfatidase |

DETAILED DESCRIPTION OF THE INVENTION AND BRIEF DESCRIPTION OF THE DRAWINGS

Figure 1B:
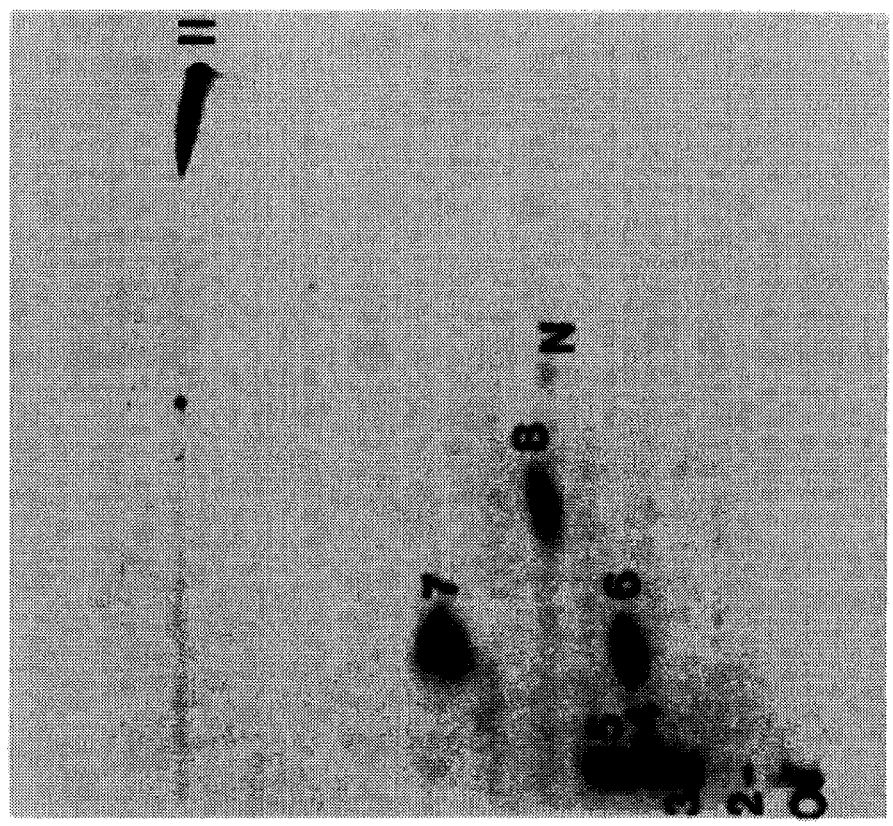
Figure 1A:
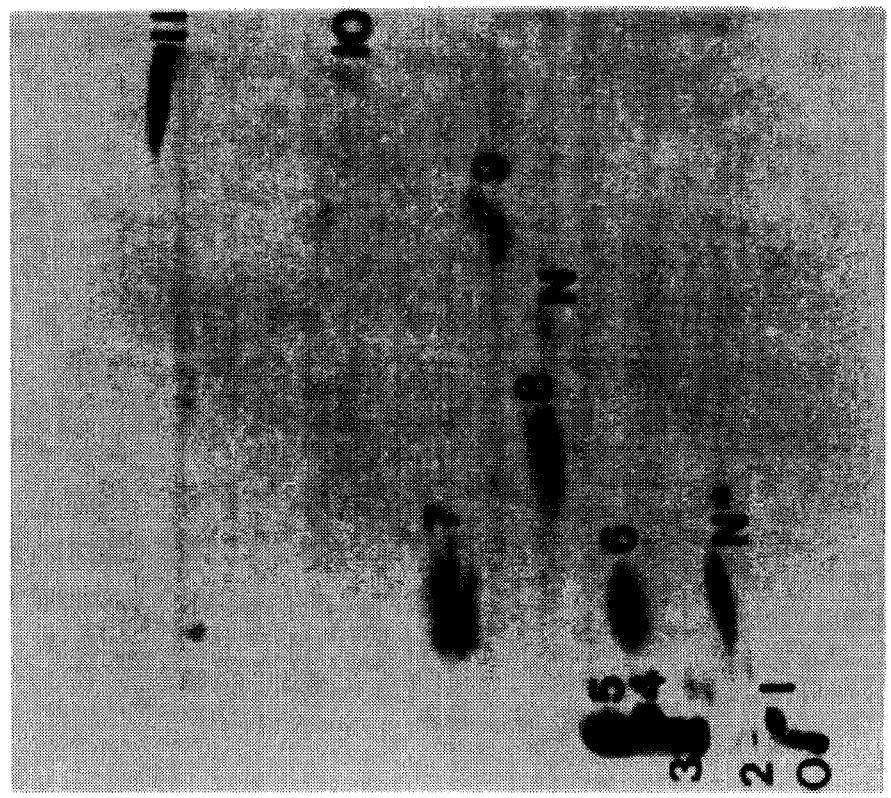

While the specification concludes with claims particularly pointing out and distinctly claiming the subject matter regarded as forming the invention, it is believed that the invention will be better understood from the following illustrative detailed description taken in conjunction with the accompanying drawings in which:

FIG. 1, in two parts A and B, shows by autoradiographic visualization the effects on glycolipid biosynthesis in HL-60 cells that were metabolically labelled with [$^{14}$C] palmitic acid, FIG. 1A: in the presence of 0.5 mM N-butyl deoxynojirimycin (+NB-DNJ) or FIG. 1B: absence of NB-DNJ (untreated -UT).

Figure 2:
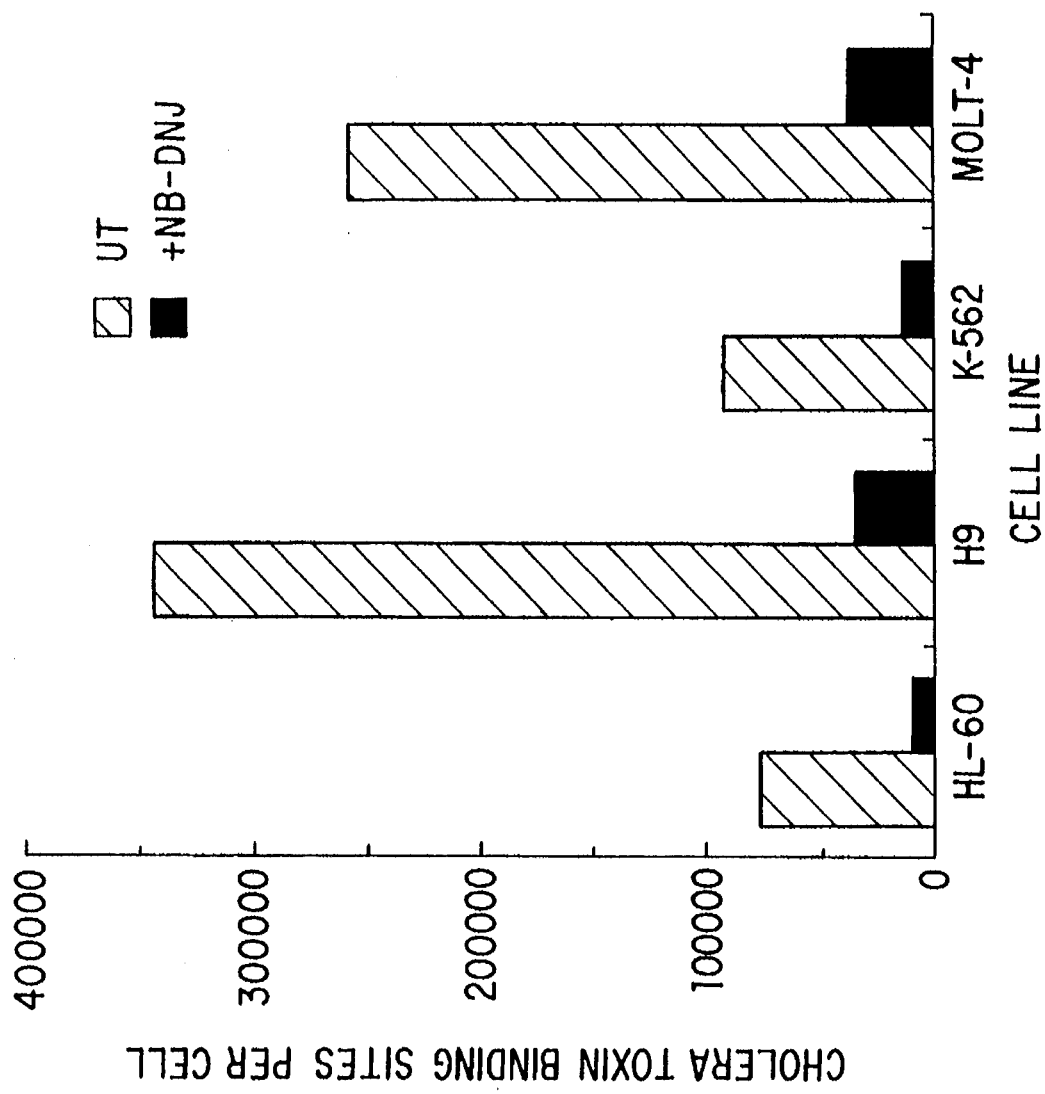

FIG. 2 is a bar chart which shows the cholera toxin binding sites per cell for four different cell lines (HL-60, H9, K-562 and MOLT-4) in which the cholera toxin was fluorescein conjugated and the levels of binding to the cell surfaces of untreated (UT) cells and cells treated with 0.5 mM N-butyl deoxynojirimycin (+NB-DNJ) were measured by flow cytometry.

Figure 3:
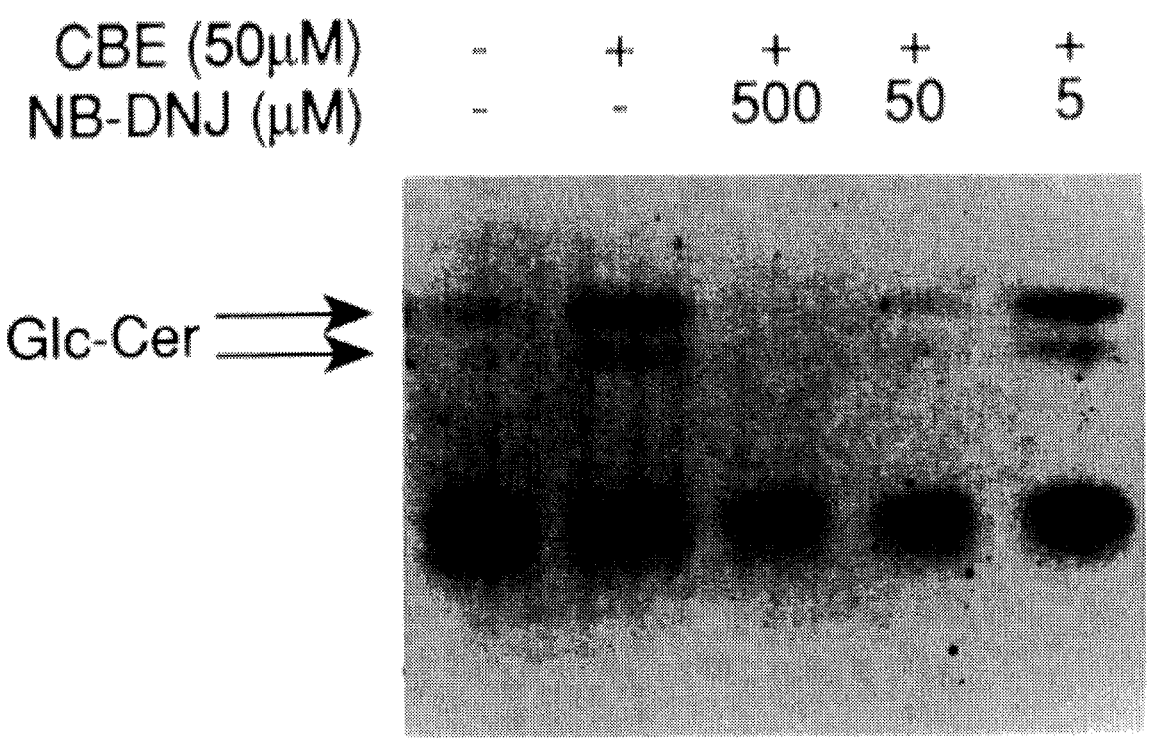
Figure 4A:
Figure 4B:
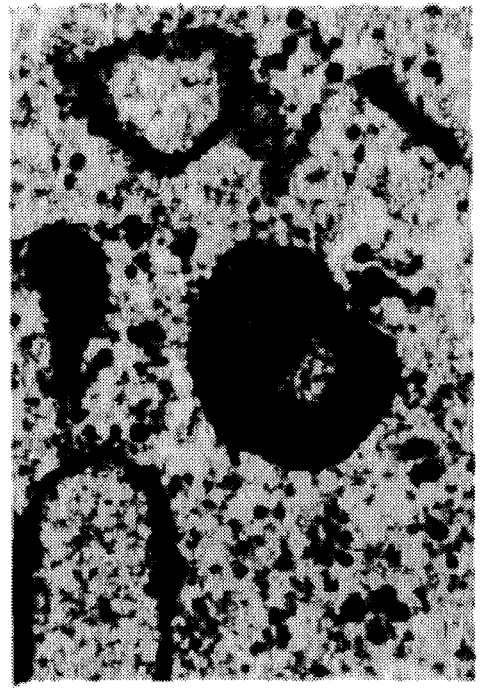
Figure 4C:
Figure 4D:

FIG. 3 shows by thin layer chromatography (TLC) the effects on WEHI-3B cells cultured in the presence (+) or absence (−) of an irreversible glucocerebrosidase inhibitor, conduritol β epoxide (CBE), to mimic the inherited disorder found in Gaucher's disease in which the cells were cultured in the presence (5 to 500 μM) or absence (−) of N-butyl deoxynojirimycin (NB-DNJ) and in which the glucosylceramide (Glc-Cer) levels were examined by TLC analysis.

FIG. 4, in four parts, A, B, C and D, shows the effects as in FIG. 3 but in which the glucosylceramide (Glc-Cer) levels were measured by transmission electron microscopy instead of TLC. FIG. 4A shows untreated representative lysosome; FIG. 4B shows lysosome treated with CBE; FIG. 4C shows lysosome treated with CBE plus 500 μM plus NB-DNJ; FIG. 4D shows lysosome treated with CBE plus 50 μM NB-DNJ. The scale bar of FIG. 4 is shown in FIG. 4D and represents 0.1 μm.

Figure 5:
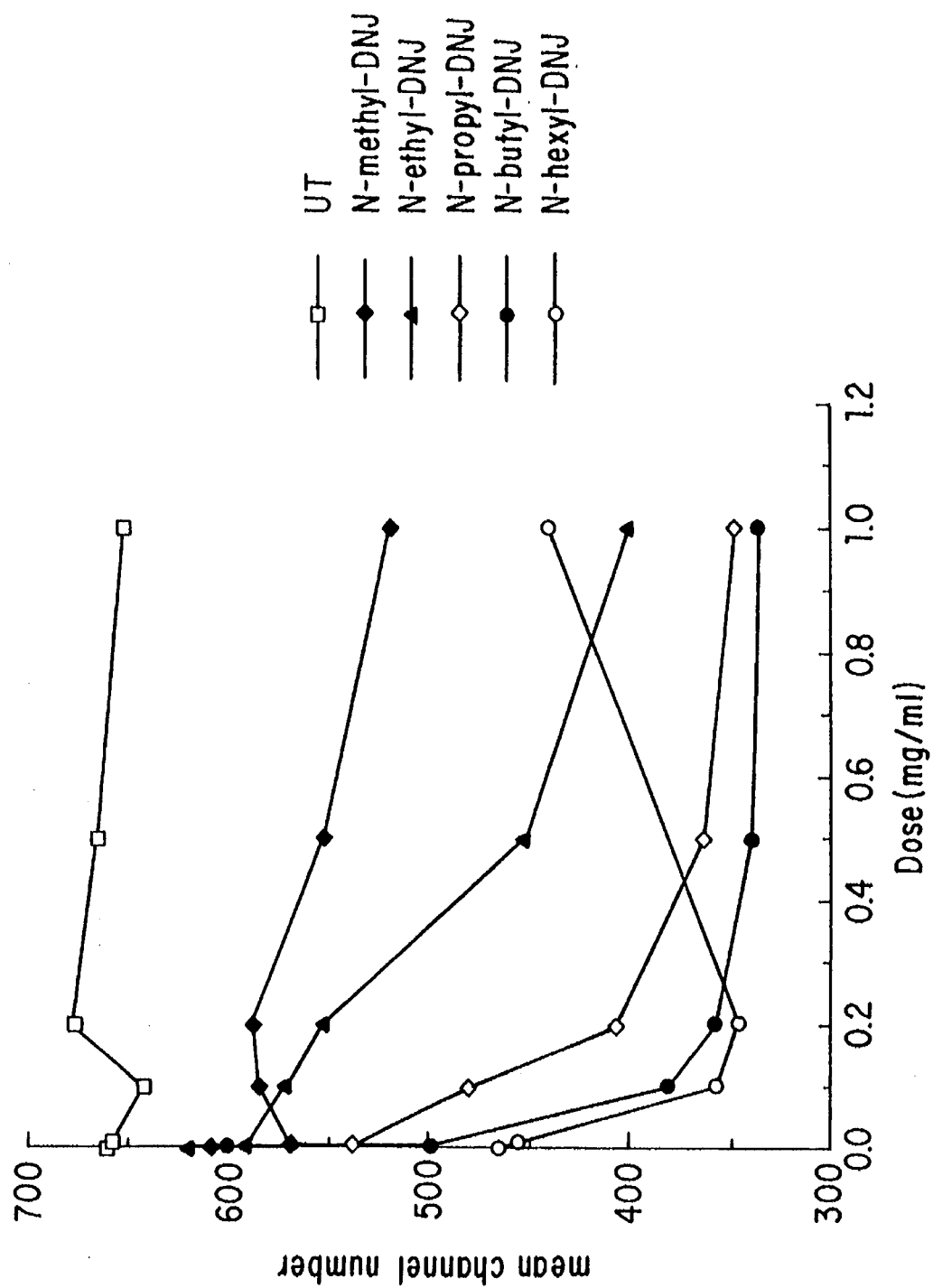

FIG. 5 is a graphical representation which shows the inhibition of cholera toxin binding in HL-60 cells cultured in the presence of various N-alkyl-DNJ compounds as indicated at a range of doses (0.0 to 1.0 mg/ml) or untreated (UT) for three days at each dose and assayed by flow cytometry following staining with FITC-cholera cholera toxin. The data are plotted as dose of compound (mg/ml) on the x-axis against mean channel fluorescence intensity (mean channel number) on the y-axis.

Figure 6D:
Figure 6C:

FIG. 6, in four parts, A, B, C and D, shows by autoradiographic visualization the effects as in FIG. 1, compared to similar treatment with PDMP or PPMP. FIG. 6A: untreated (UT); FIG. 6B: in the presence of 0.5 mM N-butyl deoxynojirimycin (NB-DNJ); FIG. 6C: in the presence of 5 μM PDMP; FIG. 6D: in the presence of 5 μM PPMP.

In order to further illustrate the invention, the following detailed examples were carried out although it will be understood that the invention is not limited to these specific examples or the details described therein.

EXAMPLE 1

To investigate the effects of the imino sugar N-butyldeoxynojirimycin (NB-DNJ) on glycolipid biosynthesis, HL-60 cells were metabolically labelled with [$^{14}$C]-palmitic acid in the presence or absence of 0.5 mM NB-DNJ. Total cellular lipids were solvent extracted and separated by two dimensional thin layer chromatography (2D-TLC) and the individual components visualized by autoradiography (FIG. 1). The major cellular phospholipid species were unaffected by NB-DNJ treatment as verified by TLC spot elution, recovery and scintillation counting. However, both the neutral glycolipids and gangliosides were absent from treated cultures (FIG. 1B). This implied that a very early step in glycolipid biosynthesis was affected by NB-DNJ treatment. To establish whether this activity was a common property of imino sugars and related compounds, a number of N-linked oligosaccharide processing inhibitors were assayed for their ability to inhibit HL-60 glycolipid biosynthesis using 2D-TLC analysis (Table 4). The glucosidase inhibitors DNJ and castanospermine, and the mannosidase inhibitors swainsonine and deoxymannojirimycin (DMJ), had no effect. When the N-alkylated derivatives of DNJ were tested the N-methyl analogue had no effect but both the N-butyl and N-hexyl analogues surprisingly inhibited the biosynthesis of glycolipids. This indicated that the length of the alkyl chain was a critical parameter for this inhibitory activity. In addition, NB-DNJ was inhibitory at relatively low compound concentrations (approximately 50 µM) indicating that this compound is a more potent inhibitor of glycolipid biosynthesis than it is as an α-glucosidase I inhibitor (mM range in cell culture systems). It is believed that the N-butyl and N-hexyl derivatives are specifically inhibiting UDP-glucose:N-acylsphingosine glucosyltransferase [Basu et al., J. Biol. Chem. 248, 1388–1394 (1973)] (EC 2.4.1.80). This transferase is pivotal in generating glucosyl ceramide (Glc-Cer) which is the precursor for the more complex glycosphingolipids and gangliosides. The inhibition of the glucosyltransferase is consistent with the uniform loss of all glycolipid species observed in the presence of the two compounds (FIG. 1). In cell free assays NB-DNJ but not DNJ inhibited the transfer of glucose from UDP-glucose to a ceramide acceptor.

EXAMPLE 2

This example illustrates that glycolipid expression at the cell surface is also inhibited in cells cultured in the presence of NB-DNJ. Four cell lines (of both myeloid and lymphoid origin) were grown in medium containing 0.5 mM NB-DNJ for three days and the level of cell surface GM1 (Galβ3GalNAcβ4(NeuAcα3)-Galβ4Glcβ3Cer) glycolipid expression was measured by flow cytometry. As a specific probe, advantage was taken of the GM1 binding specificity of the cholera toxin B chain [van Heyningen, Nature 249, 415–417 (1974); Karlsson, Ann. Rev. Biochem. 58, 309–350 (1989)]. The toxin was fluorescein conjugated and the levels of binding to the cell surface of treated and untreated cell lines was measured (FIG. 2). The number of cholera toxin binding sites per cell was determined by including fluoresceinated microbead standards in the assay. The four cell lines showed different levels of cholera toxin binding. The two myeloid cell lines (HL-60 and K-562) both expressed approximately $1 \times 10^5$ copies of cholera toxin binding sites per cell while the two lymphoid cell lines (MOLT-4 and H9) expressed approximately $2.5–5.0 \times 10^5$ copies per cell. The binding of cholera toxin to the four cell lines cultured in the presence of NB-DNJ was reduced by approximately 90% in all cases. This was consistent with the loss of GM1 from the cell surface and provided further evidence for the inhibition of glycolipid biosynthesis by NB-DNJ. It also suggests that imino sugar derivatives have use as potential anti-microbial agents by inhibiting the surface expression of glycolipid receptors for bacteria and bacterial toxins as shown in Tables 1 and 2, respectively.

EXAMPLE 3

The identification of NB-DNJ and N-hexyl DNJ as novel inhibitors of glycolipid biosynthesis offers an alternative approach for manipulating cellular glycolipid levels. The glycolipid storage disorder, Gaucher's disease, results from the autosomal inheritance of a defective glucocerebrosidase enzyme (β- D-glucosyl-N-acylsphingosine glucohydrolase, EC 3.2.1.45) which prevents the complete catabolism of Glc-Cer in the lysosome [Barranger and Ginns, The Metabolic Basis of Inherited Disease, 1677–1698 (McGraw-Hill, New York, 1989); Tybulewicz et al., Nature 357, 407–410 (1992); Beutler, Science 256, 794–799 (1992)]. However, in contrast with the impaired degradation of Glc-Cer, the rate of glycolipid biosynthesis in these individuals remains normal. As a consequence, Glc-Cer is accumulated over time leading to lysosomal storage in cells of the monocyte-macrophage system which is diagnostic of this disorder [Parkin and Brunning, Prog. Clin. Biol. Res. 95, 151–175 (1982)]. One approach for the management of this and related disorders [Neufeld, Ann. Rev. Biochem. 60, 257–280 (1991)] is to use specific inhibitors of glycolipid biosynthesis [Vunnam and Radin, Chem. Phys. Lipids 26, 265–278 (1980); Inokuchi and Radin, J. Lip. Res. 28, 565–571 (1987); Abe et al., J. Biochem. 111 191–196 (1992)] to reduce cellular glycolipid production to a level which can be completely catabolized by the defective glucocerebrosidase, thereby preventing glycolipid accumulation. This example illustrates that glycolipid storage can be prevented by NB-DNJ in an in vitro model of Gaucher's disease. The murine macrophage cell line WEHI-3B was cultured in the presence of an irreversible glucocerebrosidase inhibitor, conduritol β epoxide (CBE), to mimic the inherited disorder found in Gaucher's disease [Newburg et al., Exp. Molec. Pathol. 48, 317–323 (1988)]. WEHI-3B cells are described in Cancer Res. 37, 546–550 (1977), and are readily available from the American Type Culture Collection, Rockville, Md, under accession number ATCC TIB 68. The WEHI-3B cells were cultured in the presence or absence of NB-DNJ and glucosylceramide levels were examined by TLC analysis (FIG. 3). Following CBE treatment the cells accumulated Glc-Cer relative to untreated controls. However, in cultures containing 500 µM or 50 µM NB-DNJ, this accumulation was prevented. At the lower dose (50 µM) cultures contained Glc-Cer levels comparable to untreated controls whereas at the highest dose (500 µM) cultures contained almost undetectable levels of Glc-Cer. Cells treated with 5 µM NB-DNJ were identical to CBE treated cells demonstrating that in this in vitro Gaucher's disease model a compound dose of 50 µM NB-DNJ will prevent Glc-Cer accumulation. The lysosomes of CBE treated cultures and CBE plus NB-DNJ cultures were examined by transmission electron microscopy (FIG. 4). There was evidence of lipid accumulation in the lysosomes of CBE treated cells, FIG. 4B, relative to untreated controls, FIG. 4A, but not in CBE+NB-DNJ treated cultures FIG. 4C, 500 µM and FIG. 4D 50 µM, thereby confirming that NB-DNJ prevented CBE induced glycolipid accumulation by the partial inhibition of glycolipid biosynthesis.

The identification herein of N-alkyl derivatives of DNJ capable of modulating cellular glycolipid levels is useful for the management of several glycolipid storage disorders. These compounds affect Glc-Cer biosynthesis which is the precursor of glycolipids accumulating in many storage disorders, independent of the individual enzyme defects of these diseases (Neufeld supra). See Table 3, hereinbefore, which lists hereditary glycolipid storage disorders and their corresponding lipid accumulation and enzyme defect. In addition, these compounds have therapeutic use for the treatment of infectious disease agents which utilize cellular glycolipid receptors (Karlsson, supra) and as modulators of cell proliferation [Hakomori, Ann. Rev. Biochem. 50, 733–764 (1981); Felding-Habermann et al., Biochemistry 29, 6314–6322 (1990)], tumor growth [Inokuchi et al., Cancer Lett. 38, 23–30 (1987)] and metastasis [Inokuchi et al., *Cancer Res*, 50, 6731–6737 (1990); Mannori et al., *Int. J. Cancer* 45, 984–988 (1990)], where roles for glycolipids have been implicated.

The detailed procedures for obtaining the results of Examples 1 to 3 above, as shown by FIGS. 1 to 6 and Table 4 are as follows:

FIG. 1

Effects of NB-DNJ on total HL-60 lipid composition. Lipid identities were determined by comparison to authentic lipid standards, differential chemical detection of phospholipids and glycolipids and laserdesorption mass spectrometry analysis of the mono and dihexaside species. Lipids were assigned as follows (untreated cells, FIG. 1A—left hand panel): 1. gangliosides; 2. lysophospatidylcholine; 3. ceramide phosphorylcholine; 4. ceramide phosphorylethanolamine; 5. phospatidylcholine; 6. phosphatidylinositol; 7. phosphatidylethanolamine; 8. phosphatidylglycerol; 9. diglycosylceramide; 10. monoglycosylceramine; 11. cholesterol/fatty acids/neutral lipids; N and N, are unknowns and 0 is the sample origin. Following NB-DNJ treatment (FIG. 1B—right hand panel) species 1 (gangliosides), 9 (diglycosylceramide), 10 (monoglycosylceramide) and N* (unknown) were absent. Method: HL-60 cells were cultured (10 ml) by conventional procedures as previously described [Platt et al., *Eur. J. Biochem.* 208, 187–193 (1992)] at a seeding density of $5 \times 10^4$ cells per ml in the presence or absence of 0.5 mM NB-DNJ (G. D. Searle & Co., Skokie, Ill.) for 24 hours. For labelling and 2D-TLC, the conventional, published method of Butters and Hughes was followed [*In vitro* 17, 831–838 (1981)]. Briefly, [$^{14}$C]-palmitic acid (ICN-Flow, High Wycombe, Bucks. UK., 56.8 mCi/mmol) was added as a sonicated preparation in fetal calf serum (0.5 µCi per ml) and the cells were cultured for a further three days maintaining NB-DNJ in the cultures. The cells were harvested, washed three times with PBS and extracted in 1 ml chloroform:methanol (2:1 v/v) overnight at 4° C. The extracts were centrifuged, the chloroform:methanol extract was retained and the pellet was re-extracted as above for two hours at room temperature. Pooled extracts were dried under nitrogen and redissolved in 50 µl chloroform:methanol (2:1, v/v). One percent of the sample volume was taken for the determination of radioactivity by scintillation counting and a $1 \times 10^6$ cpm loaded as a single spot onto a 20 cm$^2$ TLC plate (Merck, BDH, Poole, Dorset, U.K.). The samples were separated in the first dimension in chloroform:methanol:water (65:25:4) and the plate dried overnight under vacuum. Separation in the second dimension was achieved using a solvent of tetrahydrofuran:dimethoxymethane:methanol:water (10:6:4:1). Plates were air dried and exposed to Hyperfilm-MP high performance autoradiography film (Amersham International, Amersham, UK).

Table 4

Effects of sugar analogues on HL-60 glycolipid biosynthesis. The data are summarized from 2D-TLC analysis on each compound at the indicated concentrations (see FIG. 1 method, above). Compounds: The synthesis of alkylated derivatives of DNJ is well known. See, e.g., Fleet et al., *FEBS Lett.* 237, 128–132 (1988). DMJ was purchased from Boehringer Mannheim (Lewes, Sussex, U.K.), swainsonine and castanospermine were obtained from Sigma (Poole, Dorset, UK). Compound doses were selected that were close to the tolerated upper limit of the individual compounds which maintained ninety percent cell viability. HL-60 cells were cultured as described in FIG. 1 procedure, above.

TABLE 4

| Compound | Dose (mg/ml) | Glycolipid Inhibition |
| --- | --- | --- |
| DNJ | 0.2 | – |
| N-methyl DNJ | 0.1 | – |
| N-butyl DNJ | 0.001 | +/– |
| " | 0.01 | + |
| " | 0.1 | + |
| N-hexyl DNJ | 0.2 | + |
| DMJ | 0.06 | – |
| Castanospermine | 0.1 | – |
| Swainsonine | 0.1 | – |

FIG. 2

Quantitative analysis of cholera toxin binding to human cell lines following three days treatment with NB-DNJ.

Methods: Cells were maintained in logarithmic phase growth in RPMI-1640 medium. Cholera toxin B chain (Sigma) was conjugated to fluorescein isothyocyanate (Sigma) and flow cytometric analysis was carried out by conventional procedure as described by Platt et al., Supra. Analysis was performed on a FACScan Cytometer (Becton Dickinson, Sunnyvale Calif., USA), Data on viable cells were collected on a four decade $\log_{10}$ scale of increasing fluorescence intensity. The data are presented as mean copy number of cholera toxin bindings sites per cell on the y-axis against the four cell line on the x-axis, in the presence or absence of 0.5 mM NB-DNJ. The specificity of cholera toxin:cell surface binding was established by inhibiting this interaction with a one hundred fold molar excess of GM1 derived oligosaccharide, GalβGalNAcβ4(NeuAcβ3)Galβ4Glcβ3Cer. Seventy to ninety percent inhibition was achieved depending on the individual cell line. A control oligosaccharide (lacto-N-tetarose) was not inhibitory.

FIGS. 3 and 4

Effects of NB-DNJ on an in vitro model of Gaucher's disease. FIG. 3: 1 dimensional TLC analysis on WEHI-3B cells treated as indicated. FIG. 4: transmission electron microscopy of WEHI-3B Gaucher cell lysosomes: A. untreated representative lysosome, B. lysosome showing extensive accumulation of dense material in the presence of CBE consistent with Glc-Cer accumulation, C. CBE plus 500 µM NB-DNJ and D. CBE plus 50 µM NB-DNJ, each of C and D showing lysosomes with normal density contents. No changes were observed in the lysosomes of cells treated with NB-DNJ alone.

Methods: The murine macrophage cell line WEHI-3B was maintained in logarithmic phase growth for 14 days in RPMI-1640 in the presence or absence of 50 µM conduritol βepoxide (CBE, Toronto Research Chemicals, Downsview, Canada) with or without NB-DNJ at the indicated concentrations. Cells were passaged every three days in the presence of the stated concentrations of compounds. Equal cell numbers ($5 \times 10^6$) were harvested, extracted as described hereinbefore (FIG. 1 procedure), separated by one dimensional TLC (first dimension solvent, FIG. 1 procedure) and visualized using β-naphthol (1% w/v in methanol) followed by 50% (v/v) sulphuric acid. Similar data were obtained using the independent mouse macrophage cell line P388D-1. These cells are described in *J. Immunol.* 114, 894–897 (1975), and are readily available from the American Type Culture collection, Rockville, Md., under accession number ATCC TIB 63. The authentic Glc-Cer standard from human Gaucher spleen (arrows) was purchased from Sigma.

Cells for electron microscopy were harvested ($1 \times 10^7$ cells per treatment), washed three times in serum free RPMI-1640 medium and fixed in medium containing 2% glutaraldehyde (v/v) on ice for two hours. Cells were washed in 0.1M cacodylate buffer containing 20 mM calcium chloride (w/v). Fixed cells were stained with 1% osmium tetroxide in 25 mM cacodylate buffer (w/v) containing 1.5% potassium ferrocyanide (w/v) for 2 hours on ice. Samples were dehydrated through an ethanol series (50, 70, 95 and 100% v/v), transferred to propylene oxide and embedded in Embed 800 (Electron Microscopy Sciences, PA, USA). The samples were polymerized at 60° C., sections cut, stained with uranyl acetate/lead citrate and observed with a Hitachi 600 microscope at 75 v.

FIG. 5

Dose response curves of cholera toxin binding to HL-60 cells following three days treatment with various N-alkyl-DNJ compounds. The test method employed for FIG. 5 was the same as for FIG. 2, above, but the data are plotted as dose of compound on the x-axis against mean channel fluorescence intensity on the y-axis. The N-methyl, N-ethyl, N-propyl, N-butyl and N-hexyl derivatives of DNJ were thus tested and compared with the untreated (UT) control sample.

FIG. 6

Effects of NB-DNJ, PDMP and PPMP on total HL-60 lipid composition. The test method employed for FIG. 6 was the same as for FIG. 1, above, but was extended to include for comparison treatment with DL-threo-1-phenyl-2-decanoylamino-3-morpholino-1-propanol (PDMP) or DL-threo- 1-phenyl-2-hexadecanoylamino-3-morpholino-1propanol (PPMP), both obtained from Matreya Inc., Pleasant Gap, Pa. FIG. 6A: untreated cells as in FIG. 1A—left panel; FIG. 6B: cells treated with 0.5 mM NB-DNJ as in FIG. 1B—right panel; FIG. 6C: cells treated with 5 μM PDMP from 10 mM stock solution in ethanol; FIG. 6D: cells treated with 5 μM PPMP from 10 mM stock solution in ethanol.

In addition to their use as antimicrobial agents and as inhibitors of glycolipid biosynthesis in cells, the inhibitory agents described herein also can be used for administration to patients afflicted with glycolipid storage defects by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human daily dosage would normally range from about one to about 100 milligrams of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, Remington's *Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed:

1. The method of inhibiting the biosynthesis of glycolipids in human cells capable of producing glycolipids comprising subjecting said cells in vitro to a glycolipid inhibitory effective amount of an N-alkyl derivative of 1,5-dideoxy-1,5-imino-D-glucitol in which said alkyl contains from 2–8 carbon atoms.

2. The method of claim 1 in which the alkyl group contains from 4–6 carbon atoms.

3. The method of claim 2 in which the alkyl group is butyl.

4. The method of claim 2 in which the alkyl group is hexyl.

5. The method of claim 1 in which the inhibitory effective amount is from about 50 μM to about 500 μM.

6. The method of claim 1 in which the glycolipid is a glucoceramide based glycosphingolipid.

7. The method of claim 1 in which the glycolipid is a lysosomal glycolipid.

* * * * *